US011752226B2

(12) United States Patent
Lucio

(10) Patent No.: US 11,752,226 B2
(45) Date of Patent: Sep. 12, 2023

(54) HANDHELD DISINFECTION DEVICE

(71) Applicant: 3B Medical, Inc., Winter Haven, FL (US)

(72) Inventor: Albert A. Lucio, Haines City, FL (US)

(73) Assignee: 3B Medical Inc., Winter Haven, FL (US)

( * ) Notice: Subject to any disclaimer, the term of this patent is extended or adjusted under 35 U.S.C. 154(b) by 62 days.

(21) Appl. No.: 16/854,985

(22) Filed: Apr. 22, 2020

(65) Prior Publication Data

US 2021/0330827 A1 Oct. 28, 2021

(51) Int. Cl.
*A61L 2/10* (2006.01)
*A61L 2/24* (2006.01)
*A61L 2/26* (2006.01)

(52) U.S. Cl.
CPC ............ *A61L 2/10* (2013.01); *A61L 2/24* (2013.01); *A61L 2/26* (2013.01); *A61L 2202/11* (2013.01); *A61L 2202/14* (2013.01); *A61L 2202/16* (2013.01)

(58) Field of Classification Search
CPC ..... A61L 2/10; A61L 2/24; A61L 2/26; A61L 2202/11; A61L 2202/14; A61L 2202/16
See application file for complete search history.

(56) References Cited

U.S. PATENT DOCUMENTS

D485,364 S  *  1/2004  Lee ............................ D26/37
7,888,657 B1    2/2011  Zadro
D652,529 S      1/2012  Eum
D841,180 S  *   2/2019  Latchman-Bloom ........ D24/217
D870,313 S  * 12/2019  Ou Yang .................... D24/217
D876,663 S      2/2020  Yellen et al.
D886,989 S      6/2020  Lucio
D898,219 S  * 10/2020  Xie ........................... D24/217
10,905,785 B2   2/2021  Lucio
(Continued)

FOREIGN PATENT DOCUMENTS

WO    WO-2013122297 A1 *  8/2013 ........... A46B 17/065

OTHER PUBLICATIONS

"COVID-19 Sanitizing Corona Virus with Handheld UVC Lights", https://www.youtube.com/watch?v=PoAi1vPVi1A, Mar. 19, 2020 (Year: 2020).*

(Continued)

*Primary Examiner* — David E Smith
(74) *Attorney, Agent, or Firm* — Carlson, Gaskey & Olds, P.C.

(57) ABSTRACT

This disclosure relates to a handheld disinfection device. The device may be used to disinfect various items and/or surfaces in home, workplace, and travel settings, as examples. The disclosed device includes a UV light source and further includes one or more protective features configured to protect the UV light source. As examples, the disclosed device may include a grille and/or a retractable shade configured to protect the UV light source. The disclosed device may also incorporate one or more safety features configured to reduce accidental exposure of a user's eyes to the UV light source, one of which is a proximity feature preventing the UV light source from activating when the device is too far from an object of disinfection. These and other benefits will be appreciated from the following description.

20 Claims, 4 Drawing Sheets

(56) References Cited

U.S. PATENT DOCUMENTS

| | | | | |
|---|---|---|---|---|
| 2004/0256581 | A1* | 12/2004 | Au | A61L 2/10 250/504 H |
| 2008/0253941 | A1* | 10/2008 | Wichers | A61L 2/10 422/186.3 |
| 2008/0260601 | A1* | 10/2008 | Lyon | B01D 53/007 422/186.3 |
| 2010/0102252 | A1* | 4/2010 | Harmon | A61L 2/10 250/492.1 |
| 2016/0367711 | A1* | 12/2016 | Zulyniak | A61L 2/10 |
| 2017/0080251 | A1* | 3/2017 | Yehezkel | H04M 1/17 |

OTHER PUBLICATIONS

Sharper Image Manual, "Travel UV Sanitizing Wand, User Guide," Item No. 205847; precise date of publication is unknown to Applicant but the document was published no later than Apr. 21, 2020.

* cited by examiner

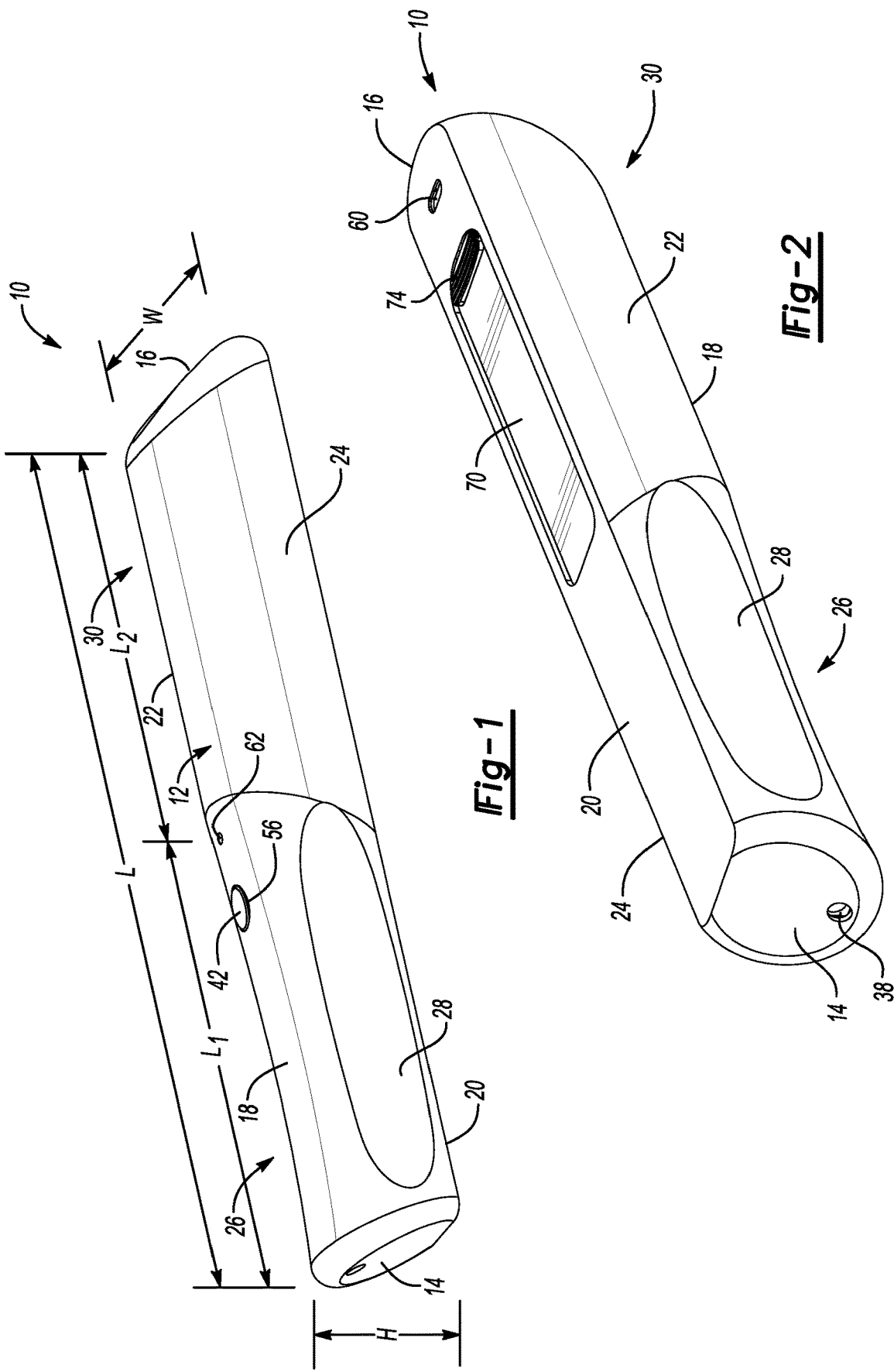

HANDHELD DISINFECTION DEVICE

TECHNICAL FIELD

This disclosure relates to a handheld disinfection device.

BACKGROUND

Handheld disinfection devices, sometimes referred to as disinfection wands or simply wands, are known. Such devices include an ultraviolet (UV) light source which, when activated, is configured to emit UV light that breaks down bacteria, germs, dust mites, mold, fungi, etc. Such devices are configured to disinfect various items and/or surfaces, both in-home and when traveling.

SUMMARY

A handheld disinfection device according to an exemplary aspect of the present disclosure includes, among other things, a body including a first portion providing a handle configured to be grasped by a hand of a user and a second portion projecting from the first portion. The second portion of the body includes a grille providing an opening including a plurality of slits. The device further includes an ultraviolet (UV) light source arranged within the second portion and configured to emit UV light out the slits.

In a further non-limiting embodiment of the foregoing handheld disinfection device, the device includes a shade selectively moveable relative to the body between a closed position in which the shade fully covers the opening and an open position in which the shade does not fully cover the opening.

In a further non-limiting embodiment of any of the foregoing handheld disinfection devices, the shade is moveable linearly in direction parallel to a length of the body.

In a further non-limiting embodiment of any of the foregoing handheld disinfection devices, an end of the shade includes tab.

In a further non-limiting embodiment of any of the foregoing handheld disinfection devices, when in the closed position, the shade covers grille.

In a further non-limiting embodiment of any of the foregoing handheld disinfection devices, the grille includes curved bars spaced-apart from one another along a length of body, and the slits are arranged between adjacent bars.

In a further non-limiting embodiment of any of the foregoing handheld disinfection devices, the device includes a power source.

In a further non-limiting embodiment of any of the foregoing handheld disinfection devices, the power source is rechargeable.

In a further non-limiting embodiment of any of the foregoing handheld disinfection devices, the device includes a controller configured to selectively activate the UV light source by directing current from the power source to the UV light source.

In a further non-limiting embodiment of any of the foregoing handheld disinfection devices, the device includes a first sensor configured to generate signal indicative of orientation of the body, and the controller only permits activation of the UV light source when the signal from the first sensor indicates a bottom surface of the body is facing a downward direction.

In a further non-limiting embodiment of any of the foregoing handheld disinfection devices, the device includes a second sensor configured to generate a signal indicative of a proximity of the body to an object of disinfection, and the controller only permits activation of the UV light source when the signal from the second sensor indicates the distance between the body and the object of disinfection is less than a threshold distance.

In a further non-limiting embodiment of any of the foregoing handheld disinfection devices, the device includes a push button on first side of body, and the controller only permits activation of the UV light source when the push button is pressed into an on position.

In a further non-limiting embodiment of any of the foregoing handheld disinfection devices, the device includes a reflector arranged within body adjacent UV light source on an opposite side of the UV light source as the grille.

In a further non-limiting embodiment of any of the foregoing handheld disinfection devices, the UV light source emits UV-C light.

In a further non-limiting embodiment of any of the foregoing handheld disinfection devices, the UV light source emits UV light at a wavelength of 254 nanometers (nm).

In a further non-limiting embodiment of any of the foregoing handheld disinfection devices, the UV light source includes a 13 Watt UV-C bulb.

A handheld disinfection device according to another aspect of the present disclosure includes, among other things, a body including a first portion providing a handle configured to be grasped by a hand of a user and a second portion projecting from the first portion. The second portion includes an opening. The device further includes an ultraviolet (UV) light source arranged within the second portion and configured to emit UV light out the opening. Additionally, the device includes a shade selectively moveable relative to the body between a closed position in which the shade fully covers the opening and an open position in which the shade at most partially covers the opening.

A handheld disinfection device according to yet another aspect of the present disclosure includes a body including a first portion providing a handle configured to be grasped by a hand of a user and a second portion projecting from the first portion. The second portion includes an opening. The device further includes an ultraviolet (UV) light source arranged within the second portion and configured to emit UV light out the opening. Additionally, the device includes a proximity sensor configured to generate a signal indicative of a distance between the body and an object of disinfection. Further, a controller is configured to activate the UV light source only when the signal from the proximity sensor indicates a distance between the body and the object of disinfection is less than a threshold distance.

BRIEF DESCRIPTION OF THE DRAWINGS

FIG. 1 illustrates an example handheld disinfection device from a top perspective.

FIG. 2 illustrates the example device from a bottom perspective. In FIG. 2, a shade is in a closed position.

In FIG. 4, the shade is in a fully open position.

In FIG. 8, the shade is in a partially open position.

DETAILED DESCRIPTION

Figure 3:
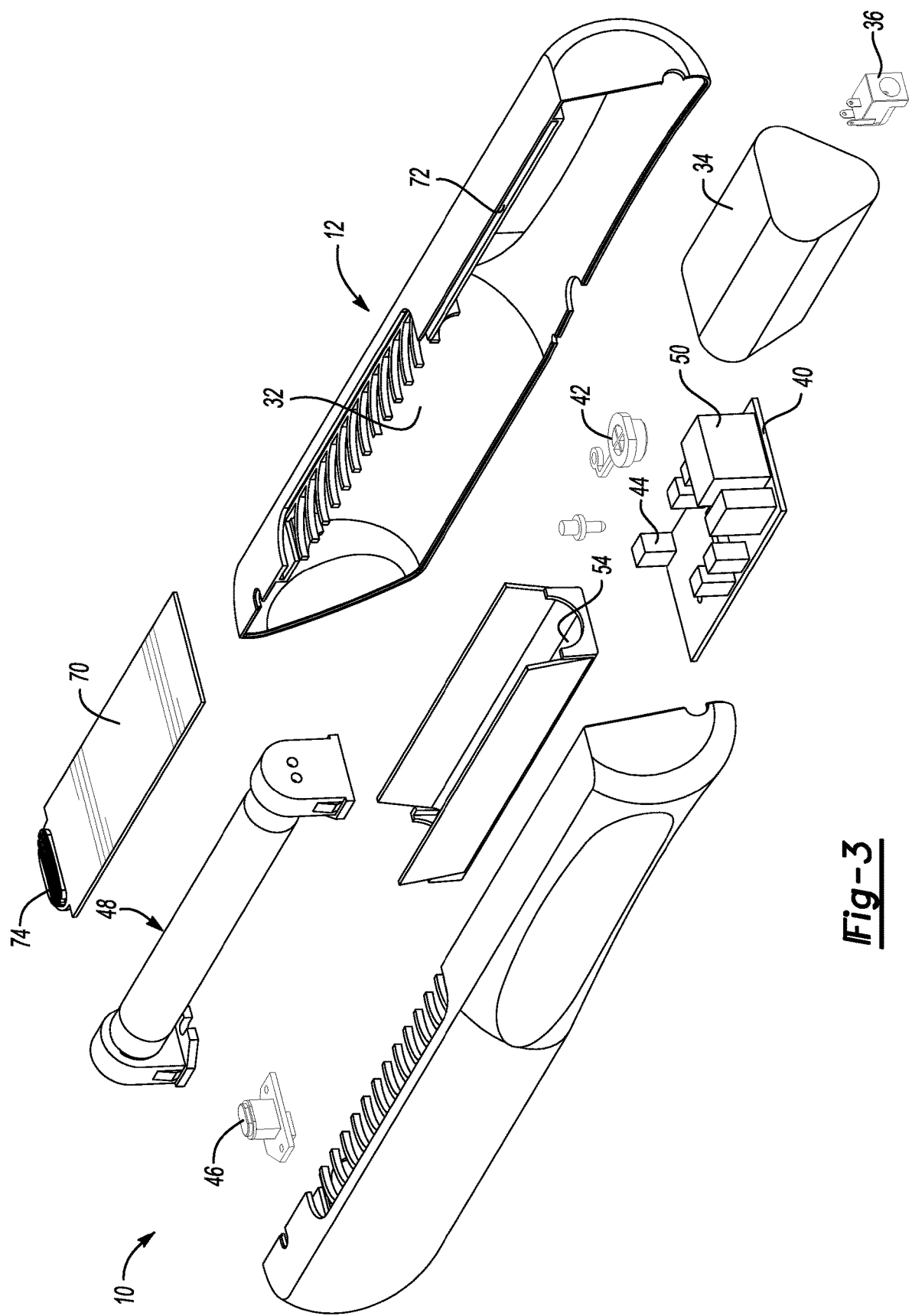
FIG. 3 is a bottom-perspective, exploded view of the example device.

This disclosure relates to a handheld disinfection device. The device may be used to disinfect various items and/or surfaces in home, workplace, and travel settings, as examples. The disclosed device includes a UV light source and further includes one or more protective features configured to protect the UV light source. As examples, the disclosed device may include a grille and/or a retractable shade configured to protect the UV light source. The disclosed device may also incorporate one or more safety features configured to reduce accidental exposure of a user's eyes to the UV light source, one of which is a proximity feature preventing the UV light source from activating when the device is too far from an object of disinfection. These and other benefits will be appreciated from the following description.

FIG. 1 is a top perspective view of an example handheld disinfection device 10 ("device 10"). FIG. 2 is a bottom perspective view of the device 10. The term handheld is used herein to refer to the device 10 being configured to be held in a hand of a user during normal use, similar to how a flashlight is held by a user during use. The device 10 may possibly be used in other applications, however, where it is used without being held in a user's hand. As will be appreciated from the below, the device 10 is portable and, to this end, is powered by a power source such as a battery within the device 10. The battery may be a rechargeable battery.

The device 10 may be used in a user's home, workplace, a hospital setting, a laboratory setting, and in other settings to disinfect a number of objects of disinfection. In this disclosure, the term object of disinfection is used to refer to an object that may be disinfected by the device 10. Example objects of disinfection include items or surfaces, including surfaces or items in homes, workplaces, hotels, airports, hospitals, laboratories, etc. Example items include medical, dental, and hygiene-related products, such as toothbrushes, hearing aids, dentures, pacifiers, clothes, etc. Example surfaces include countertops, furniture, desks, beds, pillows, etc. The device 10 may also be used to disinfect medical equipment such as components of continuous positive airway pressure (CPAP) devices, surgical devices, masks, etc.

With reference to FIGS. 1 and 2, the device 10 includes a body 12 which extends along a length L between a first end 14 and a second end 16 opposite the first end 14. The body 12 may be made of a plastic material in one example. The body 12 also exhibits a height H between a top surface 18 and a bottom surface 20. The terms "top" and "bottom" herein refer to the orientation of the device 10 from the perspective of a user when the device 10 is in use. Finally, the body 12 exhibit a width W between opposed first and second side surfaces 22, 24.

Beginning at the first end 14 and extending along a first length $L_1$, the body 12 includes a first portion 26 which provides a handle and is configured to be grasped by a hand of a user. In this example, the first and second side surfaces 22, 24 include grips 28, which may be made of an elastomeric material, within the first portion 26 to increase the ease of gripping the device 10. The first length $L_1$ corresponds to the size of a hand of an average person, and may be about half of the length L. In another example the first length $L_1$ is less than half of the length L. In a particular example, the first length $L_1$ is about 40% of the length L.

Between the end of the first length $L_1$ and the second end 16, the body 12 includes a second portion 30 along a second length $L_2$. The second length $L_2$ is the difference between the length L and the first length $L_1$. The second portion 30 projects from the first portion 26. Specifically, when the device 10 is held by a user, the second portion 30 projects distally, away from the user, relative to the first portion 26. As will be explained in more detail below, an ultraviolet (UV) light source is arranged within the second portion.

With reference to FIG. 2, the bottom surface 20 is the bottom-most surface of the device 10 and is substantially flat and planar in this example. In this way, when the bottom surface 20 rests against a surface, such as when the device 10 is not in use, the device 10 resists rolling.

FIG. 3 is an exploded view of the device 10 and illustrates an example arrangement of electrical, mechanical, and electro-mechanical components of the device 10, which, when the device 10 is assembled, are arranged within a cavity 32 within the body 12. The body 12 is split in half along its length in FIG. 3. To this end, the body 12 could be formed by connecting two halves, such as those shown in FIG. 3. However, the body 12 could be formed in another manner, such as by additive manufacturing. In the case where the body 12 is formed by connecting two halves, those halves could each be injection molded or formed by some other technique and then connected together using an adhesive or some other known connection method.

In general, within the first portion 26 of the body 12, the device 10 includes a power source 34, such as one or more batteries, configured to selectively deliver power to a UV light source under certain conditions, as discussed below. The power source 34 may be rechargeable via an interface 36, which is aligned with an opening 38 in the first end 14 (FIG. 2). The interface may be a USB or DC charging port, as examples.

The device 10 further includes a printed circuit board (PCB) 40. The PCB 40 is electrically connected to each of the various electrical and electro-mechanical components of the device 10, in this example. In particular, the PCB 40 is electrically connected to at least the power source 34, a button 42, a first sensor 44, a second sensor 46, a UV light source 48, and a controller 50.

In this example, the first sensor 44 and the controller 50 are mounted to the PCB 40. The first sensor 44 need not be mounted to the PCB 40 in all examples. Further, in this example, the second sensor 46 is not mounted to the PCB 40, but the second sensor 46 could be mounted to the PCB 40 in other examples.

The controller 50 (sometimes called a "control unit") may be programmed with executable instructions for interfacing with and operating the various components of the device 10, including but not limited to those shown in the figures and discussed herein. It should also be understood that the controller 50 may additionally include a combination of hardware and software, and specifically may include a processing unit and non-transitory memory for executing the various control strategies and modes of the device 10.

The UV light source 48, in this example, is arranged within the cavity 32 within the second portion 30 of the device 10, and is configured to emit UV light out an opening 52 (FIG. 4) formed in the bottom surface 20. In this disclosure, the UV light source 48 includes a UV-C bulb (sometimes called a "UV lamp"), such as a 13 Watt UV-C bulb configured to emit UV-C light. In other examples, the UV light source 48 is provided by a bulb within a range of 5 to 20 Watts. The UV light source 48 is configured to emit UV light having a wavelength within a range of 245-290 nanometers (nm) in one example, and in a specific example at a wavelength of wavelength of 254 nanometers (nm). UV-C light is a subtype of UV light especially suited for disinfection and is known to kill, break down, and/or inactivate microorganisms such as bacteria, germs, dust mites, mold, fungi, etc.

The opening 52 is aligned with the UV light source 48. On an opposite side of the UV light source 48 as the opening 52, a reflector 54 is arranged in the cavity 32. The reflector 54 directs UV light emitted from the UV light source 48 to the opening 52 such that a majority, if not substantially all, light emitted from the UV light source 48 is directed out the opening 52.

In general, the UV light source 48 is configured to be activated (i.e., turned on) by the controller 50 (i.e., the controller 50 permits current to flow from the power source 34 to the UV light source 48) when a user presses button 42 and when at least one other condition is present. The button 42 extends partially through an opening 56 in the top surface 18 of the body 12. The button 42 is arranged such that when a user grasps the first portion 26, the thumb of the user is located close to the button 42. The controller 50 is configured to receive signals from the button 42 regarding whether the button has been pressed or not.

In this disclosure, in order to prevent undesired exposure of a user's eyes to UV light, the controller 50 considers the signal from the button 42 and also considers one or more additional signals before activating the UV light source 48. In particular, in this disclosure, the controller 50 considers signals from the first sensor 44 and the second sensor 46.

Figure 5:
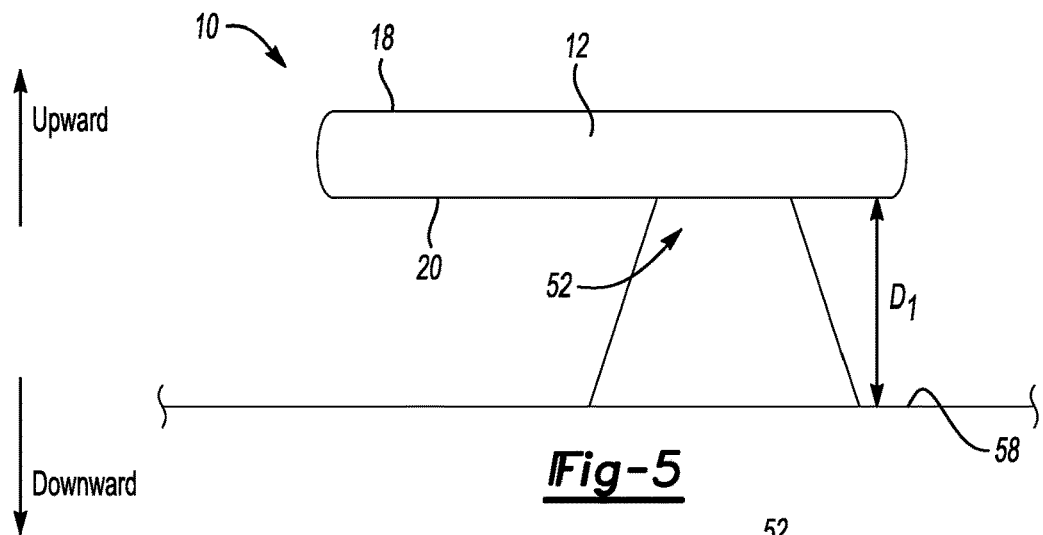
FIG. 5 schematically illustrates the device in a first orientation and at a first distance from an object of disinfection.
Figure 6:
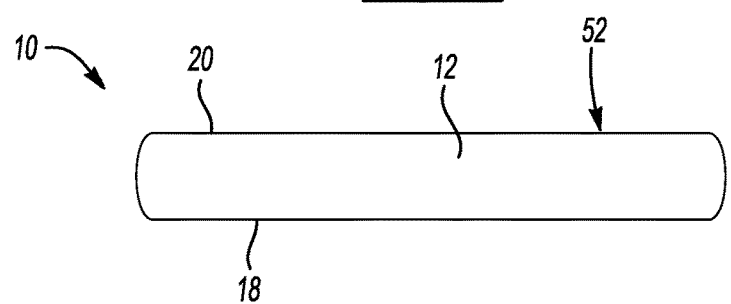
FIG. 6 schematically illustrates the device in a second orientation relative to the object of disinfection.

In an example, the first sensor 44 is configured to generate a signal indicative of orientation of the body 12. In particular, the first sensor 44 is configured to generate a signal that the controller 50 can interpret as whether the bottom surface 20 is facing downward or upward. Here, "downward" refers to a direction toward a floor or ground surface, and is in the same direction as the direction of acceleration due to gravity. When facing the downward direction, the bottom surface 20, and in turn the UV light source 48 and opening 52, are facing an object of disinfection 58 (FIG. 5). In this example, the controller 50 is configured such that the UV-light source 48 is only activated when the signal from the first sensor 44 indicates the bottom surface 20 of the body 12 is facing a downward direction, as in FIG. 5. When the bottom surface 20 faces the upward direction, as in FIG. 6, the controller 50 deactivates the UV-light source 48.

The second sensor 46 is configured to generate a signal indicative of a proximity of the body 12 to the object of disinfection 58. The second sensor 46 is arranged distal of the opening 52, in this example, and is aligned with an opening 60 (FIG. 2) in the bottom surface 20. The second sensor 46 may be provided by a known type of proximity sensor, such as an optical sensor, photoelectric sensor, or inductive sensor, as examples. In this example, the controller 50 is configured such that it only permits activation of the UV light source 48 when the signal from the second sensor 46 indicates the distance between the body 12 and the object of disinfection 58 is less than a threshold distance.

Figure 7:
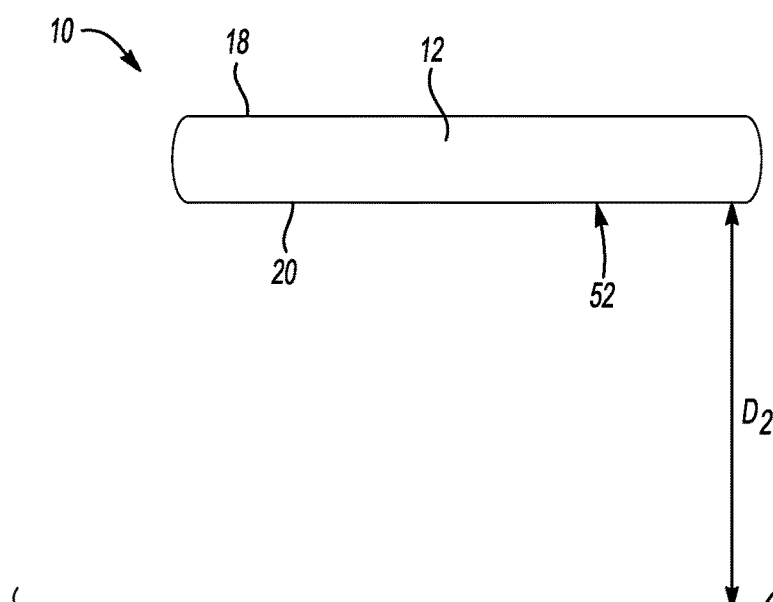
FIG. 7 schematically illustrates the device in the first orientation and at a second distance, which is greater than the first distance, from the object of disinfection.

In FIG. 5, for example, the opening 52 is facing downward, toward an object of disinfection 58, and the body 12 is spaced-apart from the object of disinfection 58 by a distance $D_1$ which is less than a threshold distance, which may be a predefined threshold distance. Further, in FIG. 5, a user has pressed the button 42, and thus the controller 50 activates the UV light source 48. In FIG. 7, however, the body 12 has moved a distance D2 from the object of disinfection which is greater than the threshold distance. Accordingly, in FIG. 7, the controller 50 deactivates the UV light source 48 despite the button 42 may pressed to an "on" position and the bottom surface 20 facing downward.

In an aspect of this disclosure, the controller 50 is configured to reactivate the UV light source 48 when a condition preventing activation of the UV light source 48 resolves. In particular, the controller 50 is configured to do so without the user needing to re-press the button 42. As an example, if the user presses the button 42 such that the button 42 is in the "on" position, and the opening 52 is facing downward, and the body 12 is within the threshold distance of the object of disinfection, then the controller 50 activates the UV light source 48. If the user momentarily moves the body 12 outside the threshold distance or inverts the body 12 such that the opening 52 faces upward, the controller 50 will deactivate the UV light source 48. When the user moves the body 12 back within the threshold distance and orients the opening 52 downward, then the controller 50 will automatically reactivate the UV light source 48. In this way, the user does not need to repeatedly press the button 42 if the UV light source 48 deactivates. The user simply needs to move the device 10 back into a proper orientation and/or position. In order to turn the UV light source 48 off, the user presses the button 42. A user may be alerted to the status of the UV light source 48 via an LED light 62 in the top surface 18.

While the device 10 includes both the first and second sensors 44, 46, this disclosure extends to devices including only one of the first and second sensors 44, 46. That said, the device 10 has added benefits with both types of sensors.

The body 12 may also incorporate one or more protective features configured to protect the UV light source 48 from damage. In an example, the body 12 does not include or support a transparent glass or plastic portion configured to prevent the UV light source 48 from damage, as such a structure may scratch and obscure the UV light source 48 over time.

In one example, the body 12 includes a grille 64 providing the opening 52 such that the opening 52 includes a plurality of slits 66 between adjacent bars 68 of the grille 64. When activated, the UV light source 48 emits light out of the slits 66. The bars 68 are curved such that an apex of the bars 68 is at a center point, which is within a plane passing through a centerline of the body 12 and extending normal to the bottom surface 20, between adjacent sides of the opening 52. The bars 68 are spaced-apart from one another in the direction of the length L such that the UV light source 48 is sufficiently protected and without obscuring a significant portion of the light emitted from the UV light source 48. The bars 68 may be integrally formed with the remainder of the body 12, such as in an injection molding step.

Additionally or alternatively, the body 12 may also incorporate a shade 70 selectively moveable to cover and uncover the opening 52. In FIG. 2, the shade 70 is in a closed, or fully closed, position in which the shade 70 covers the entirety of the opening 52 and such that the UV light source 48 is completely obscured by the shade 70. In this example, the shade 70 also covers the grille 64. The shade 70 is moveable linearly, in the direction of the length L, by sliding into a recess 72 (FIG. 3), which is adjacent the bottom surface 20 and arranged in the cavity 32. A user may slide the shade 70 using their thumb of finger, for example, and engaging their thumb/finger with a tab 74, which includes a textured surfaced in this example, at the distal end of the shade 70.

Figure 8:
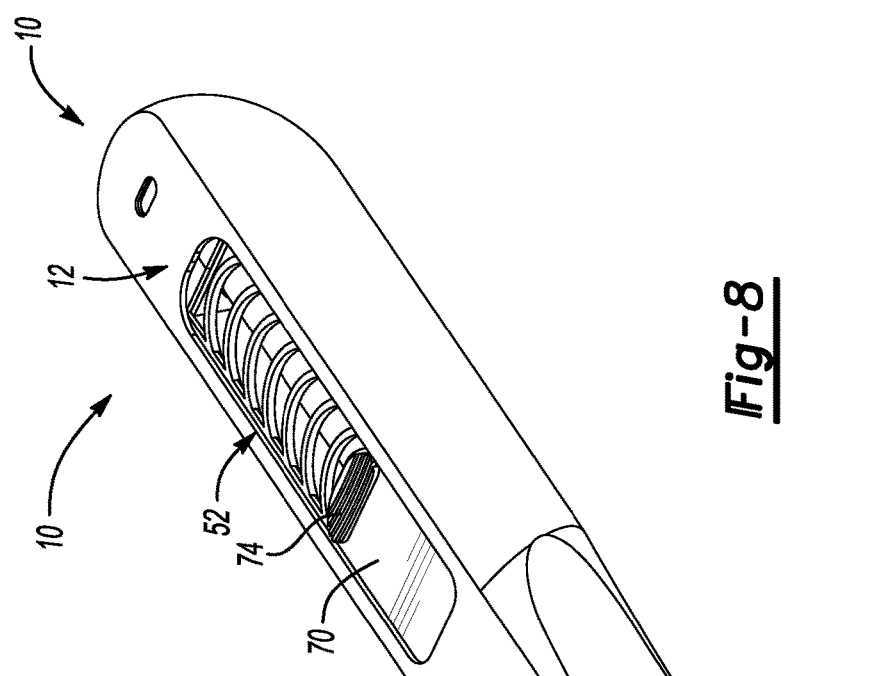
FIG. 8 illustrates the example device from a bottom perspective.
Figure 4:
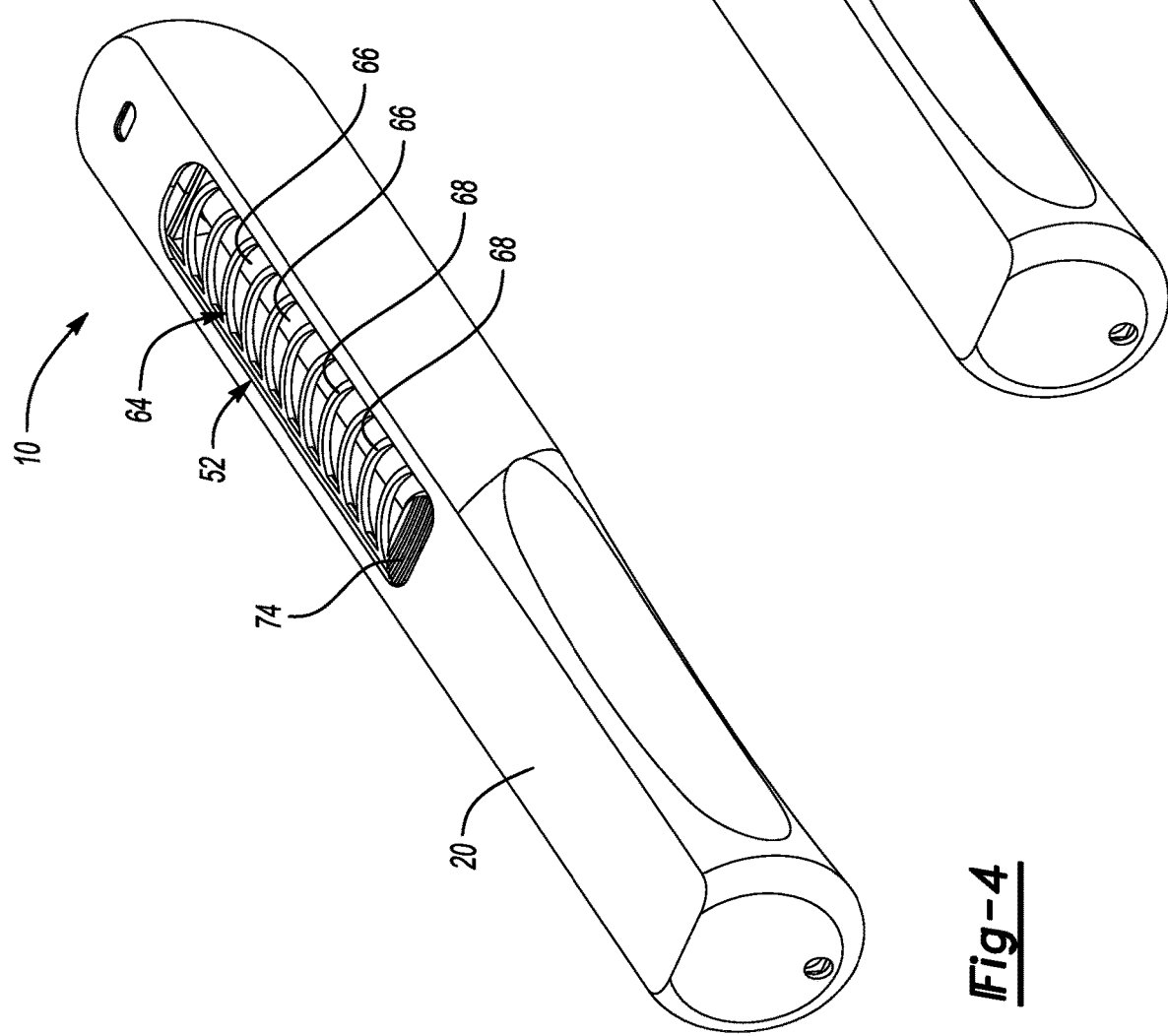
FIG. 4 illustrates the example device from a bottom perspective.

The shade 70 is moveable from the fully closed position of FIG. 2 to one or more open positions in which the shade 70 does not fully cover the opening 52. FIG. 8 illustrates the shade 70 in a partially open position in which the shade 70 obscures only a portion of the opening 52 and permits UV light to pass through the remainder of the opening 52. FIG. 4 illustrates the shade 70 in a fully open position. In FIG. 4, only the tab 74 overlaps the opening 52, and the remainder of the shade 70 is in the recess 72. The opening 52 may be sized such that, in the position of FIG. 4, the tab 74 does not overlap the UV light source 48. In FIG. 4 a vast majority of the opening 52 is unobscured by the shade 70. While in FIG. 4 the tab 74 overlaps a portion of the opening 52, the position of FIG. 4 may be referred to as a fully open position.

Directional terms such as "top," "bottom," "upward," "downward," etc., are used herein for purposes of explanation and with reference to the orientation of components illustrated in the drawings. Such directional terms should not be considered limiting. Further, it should be understood that terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A handheld disinfection device, comprising:
   a body including a first portion providing a handle with a curved side configured to be grasped by a hand of a user, a second portion projecting from the first portion that includes a grille providing an opening including a plurality of slits, and a flat, planar bottom surface opposite to the curved side;
   an ultraviolet (UV) light source arranged within the second portion and configured to emit UV light out the slits;
   a controller configured to selectively activate the UV light source by directing current from a power source to the UV light source;
   a sensor configured to generate a signal indicative of a proximity of the body to an object;
   wherein the controller is configured to only permit activation of the UV light source when the signal from the sensor indicates a distance between the body and the object is less than a threshold distance;
   wherein the handheld disinfection device is configured such that a user can hold and support the entire handheld disinfection device using a single hand while using the device to sanitize the object without the handheld disinfection device contacting the object;
   wherein the bottom surface provides a bottom-most surface of the handheld disinfection device, and is configured to resist rolling of the handheld disinfection device when the bottom surface rests against another surface;
   wherein the curved side exhibits a contour different than the bottom surface;
   wherein the grille includes a plurality of bars spaced-apart from one another in a direction of a length of the handheld disinfection device such that at least some of the slits are arranged between adjacent bars; and
   wherein the plurality of bars each include a flat bottom surface located in a common plane.

2. The handheld disinfection device as recited in claim 1, further comprising a push button on a first side of body, and wherein the controller only permits activation of the UV light source when the push button is pressed into an on position.

3. The handheld disinfection device as recited in claim 1, further comprising a reflector arranged within a body adjacent the UV light source on an opposite side of the UV light source as the grille.

4. The handheld disinfection device as recited in claim 1, wherein the UV light source emits UV-C light.

5. The handheld disinfection device as recited in claim 4, wherein the UV light source emits UV light at a wavelength of 254 nanometers (nm).

6. The handheld disinfection device as recited in claim 4, wherein the UV light source includes a 13 Watt UV-C bulb.

7. The handheld disinfection device as recited in claim 2, wherein:
   when the push button is in the on position and when the signal from the sensor indicates the distance between the body and the object is greater than the threshold distance, the controller is configured to deactivate the UV light source, and
   when the push button is in the on position and when the UV light source is deactivated based on the signal from the sensor, the controller is configured to reactivate the UV light source without requiring a user to again press the push button to the on position when the signal from the sensor indicates the distance between the body and the object is less than the threshold distance.

8. The handheld disinfection device as recited in claim 1, wherein:
   the handheld disinfection device exhibits an overall length between a first end of the body and a second end of the body, and
   the first portion exhibits a length of about half the overall length.

9. The handheld disinfection device as recited in claim 1, wherein:
   the UV light source is a single UV light source configured to emit light out each of the plurality of slits.

10. The handheld disinfection device as recited in claim 1, wherein each of the bars are curved such that each of the bars exhibits an apex at a respective center point and within a plane passing through a centerline of the body.

11. The handheld disinfection device as recited in claim 1, wherein the handheld disinfection device is configured to emit light in only one direction.

12. The handheld disinfection device as recited in claim 1, wherein:
   the sensor is a first sensor,
   the handheld disinfection device further comprises a second sensor configured to generate a signal indicative of orientation of the body, and the controller is configured to only permit activation of the UV light source when the signal from the second sensor indicates a bottom surface of the body is facing a downward direction.

13. A handheld disinfection device, comprising:
a body including a first portion providing a handle configured to be grasped by a hand of a user, and a second portion projecting from the first portion that includes an opening;
an ultraviolet (UV) light source arranged within the second portion and configured to emit UV light out the opening;
a proximity sensor configured to generate a signal indicative of a distance between the body and an object;
a controller configured to activate the UV light source only when the signal from the proximity sensor indicates a distance between the body and the object is less than a threshold distance;
wherein the handheld disinfection device is configured such that a user can hold and support the entire handheld disinfection device using a single hand while using the device to sanitize the object without the handheld disinfection device contacting the object;
wherein a bottom surface of the first portion and a bottom surface of the second portion both lie in a common plane and establish a bottom-most surface of the handheld disinfection device;
wherein the bottom-most surface is a flat, planar surface that lies in the common plane and spans an entire length of a bottom side of the handheld disinfection device; and
wherein the opening is formed in the bottom-most surface.

14. The handheld disinfection device as recited in claim 1, wherein the grille and the slits are formed in the bottom surface.

15. The handheld disinfection device as recited in claim 14, wherein the only passageway through which UV light can emit out of the handheld disinfection device is the opening of the grille.

16. The handheld disinfection device as recited in claim 1, wherein the grille is integrally formed with the body.

17. The handheld disinfection device as recited in claim 1, wherein the bottom surface of the body is defined in a first plane, and normal vectors of the first plane and the common plane are parallel.

18. The handheld disinfection device as recited in claim 1, wherein the flat, planar bottom surface of the body includes a bottom surface of the first portion and a bottom surface of the second portion.

19. A handheld disinfection device, comprising:
a body including a first portion providing a handle configured to be grasped by a hand of a user and a second portion projecting from the first portion, wherein the second portion of the body includes a grille providing an opening including a plurality of slits;
an ultraviolet (UV) light source arranged within the second portion and configured to emit UV light out the slits;
a controller configured to selectively activate the UV light source by directing current from a power source to the UV light source;
a sensor configured to generate a signal indicative of a proximity of the body to an object,
wherein the controller is configured to only permit activation of the UV light source when the signal from the sensor indicates a distance between the body and the object is less than a threshold distance,
wherein the handheld disinfection device is configured such that a user can hold and support the entire handheld disinfection device using a single hand while using the device to sanitize the object without the handheld disinfection device contacting the object,
wherein the grille includes a plurality of bars spaced-apart from one another in a direction of a length of the handheld disinfection device such that at least some of the slits are arranged between adjacent bars,
wherein the handheld disinfection device further comprises a shade selectively moveable relative to the body between a closed position in which the shade fully covers the opening and an open position in which the shade does not fully cover the opening,
wherein the shade is moveable linearly in a direction parallel to a length of the body,
wherein an end of the shade includes tab, and
wherein, when in the closed position, the shade covers the grille.

20. The handheld disinfection device as recited in claim 13, further comprising:
a sensor configured to generate a signal indicative of orientation of the body, and
wherein the controller is configured to only permit activation of the UV light source when the signal from the sensor indicates a bottom surface of the body is facing a downward direction.

* * * * *